United States Patent [19]
Lynch et al.

[11] Patent Number: 5,777,123
[45] Date of Patent: Jul. 7, 1998

[54] PROCESS FOR REGIOSELECTIVE SUBSTITUTION OF TRIFLUOROBENZOATE OR TRIFLUOROBENZONITRILE

[75] Inventors: Joseph E. Lynch, Plainfield; Yao-Jun Shi, Edison; Kenneth M. Wells, Somerville, all of N.J.

[73] Assignee: Merck & Co., Inc., Rahway, N.J.

[21] Appl. No.: 806,502

[22] Filed: Feb. 27, 1997

Related U.S. Application Data

[60] Provisional application No. 60/012,641 Mar. 1, 1996.

[51] Int. Cl.[6] .................. C07D 211/44; A61K 31/445
[52] U.S. Cl. .................. 546/216; 514/327; 514/331; 546/230; 546/238
[58] Field of Search .................. 546/216, 230, 546/238; 514/327, 331

[56] References Cited

U.S. PATENT DOCUMENTS 4,684,734  8/1987  Kaieda et al. .................. 546/345
5,332,851  7/1994  Kumai et al. .................. 558/329

OTHER PUBLICATIONS

Wells, K. M. et al.: Regioselective Nucleophilic Substitutions of Fluorobenzene Derivatives. Tetrahedron Letters. vol. 37, pp. 6439–6442, 1996.

*Primary Examiner*—C. Warren Ivy
*Assistant Examiner*—Charanjit S. Aulakh
*Attorney, Agent, or Firm*—Melvin Winokur; Richard S. Parr

[57] ABSTRACT

The invention provides a process for regioselective substitution of trifluorobenzoate/trifluorobenzonitrile to afford the difluorobenzoate/difluorobenzonitrile in good yields. The resulting difluorobenzoate/difluorobenzonitrile can again be regioselectively substituted with a second nucleophile to give monofluorobenzoate/monofluorobenzonitrile also in good yields. This process is particularly useful for forming key intermediates in the synthesis of oxytocin antagonist compounds.

5 Claims, No Drawings

PROCESS FOR REGIOSELECTIVE SUBSTITUTION OF TRIFLUOROBENZOATE OR TRIFLUOROBENZONITRILE

CROSS-REFERENCE TO RELATED APPLICATIONS

This is a non-provisional application based on provisional application, Ser. No. 60/012,641, filed Mar. 1, 1996.

FIELD OF THE INVENTION

The present invention provides a process for regioselective substitution of trifluorobenzoate and/or trifluorobenzonitrile. More particularly, regioselective nucleophilic substitution of 2,4,5-trifluorobenzoate/trifluorobenzonitrile at the 4-position yields 2,5-difluorobenzoate/difluorobenzonitrile in high yields. Subsequent substitution of the 2,5-difluorobenzoate/difluorobenzonitrile at the 2-position provides 5-fluorobenzoate/fluorobenzonitrile in good yields.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that an oxytocin antagonist would be the ideal tocolytic agent. In the last few years, evidence has accumulated to strongly suggest that the hormone oxytocin may be a physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. An oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

It is also believed that an oxytocin antagonist compound would also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea than current regimens. An additional use for oxytocin antagonists is for stopping labor prior to cesarean delivery.

A number of potent, nonpeptide benzoxazinone oxytocin antagonists have recently been identified (see PCT International Application Publication No. WO95/02405, published Jan. 26, 1995). Related compounds in the benzoxazinone series of oxytocin antagonists which are fluorinated on the central aromatic ring, for example Compound A shown below, are also potent oxytocin antagonists.

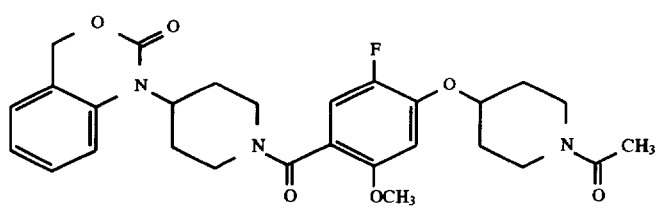

Compound A

A key intermediate in the synthesis of Compound A, and other fluorine containing structurally related oxytocin antagonist compounds, is the compound 5

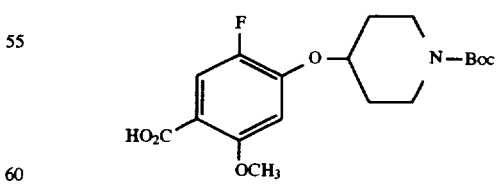

In the past, synthesis of intermediate 5 was accomplished by the direct fluorination of methyl-2,4-dihydroxylbenzoate or its analogs with N-fluoro-3,5-dichloropyridinium triflate which produced the desired 5-fluorobenzoate in low yields (ca. 30%), along with the undesired 3-fluorobenzoate. See Schemes 1 and 2 below.

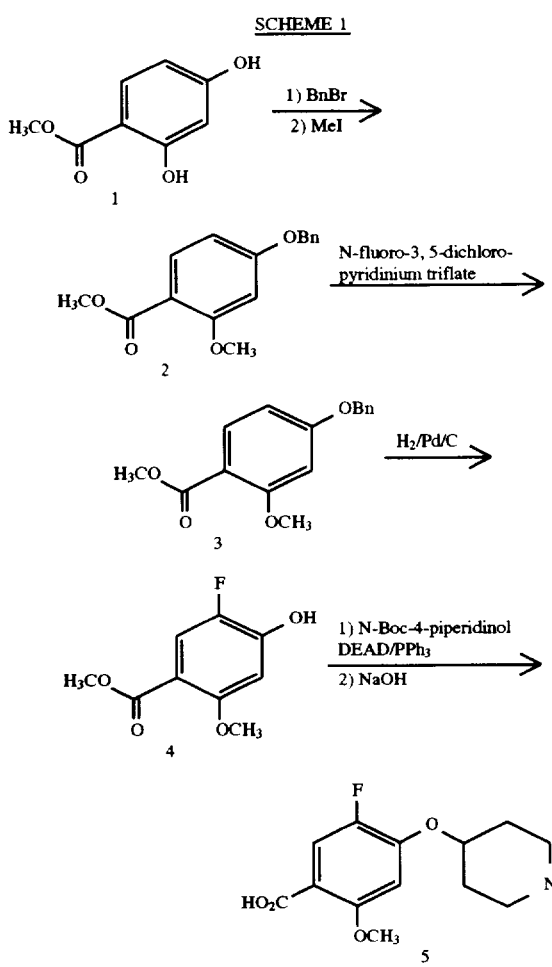

and therefore, very expensive. Thus, a need remains for a more efficient synthesis of key intermediate 5.

It has now been found that regioselective nucleophilic substitution of trifluorobenzonitrile/trifluorobenzoate provides a more efficient and less expensive route to the desired intermediate 5 in the synthesis of oxytocin antagonists useful for preterm labor, dysmenorrhea and stopping labor prior to cesarean delivery.

SUMMARY OF THE INVENTION

The present invention provides a process for forming a difluoro compound I comprising reacting a trifluoro compound II with a nucleophilic agent $R^1$ to obtain the difluoro compound I wherein Y is selected from CN or $CO_2$—$C_{1-6}$ alkyl;

$R^1$ is selected from $OR^3$, $SR^3$, CN, C≡$CR^4$, or a 4, 5, 6 or 7-membered monocyclic nitrogen containing heterocyclic ring containing one or two nitrogen atoms;

$R^3$ is selected from $C_{1-10}$ alkyl, $C_{3-8}$ cycloalkyl, phenyl-$C_{1-6}$ alkyl, phenyl or a 4, 5, 6 or 7-membered monocyclic nitrogen containing heterocyclic ring containing one or two nitrogen atoms wherein the nitrogen containing heterocyclic ring is either unsubstituted or substituted with $R^5$ and $R^6$;

$R^4$ is $C_{1-10}$ alkyl; and $R^5$ and $R^6$ are each independently selected from $CO_2R^4$, $COR^4$ or $C_{1-10}$ alkyl.

In one embodiment of the present invention is the process wherein the trifluoro compound is selected from Flash chromatography was then necessary in order to remove the undesired 3-fluorobenzoate. In addition, the supply of N-fluoro-3,5-dichloropyridinium triflate is limited, and the difluoro compound is selected from

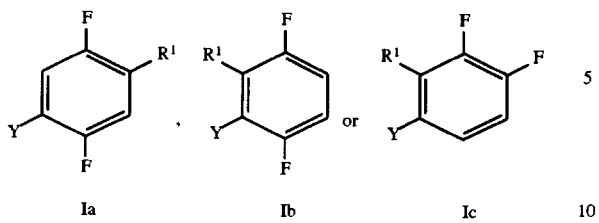

wherein all variables are as described above.

In a class of the invention is the process wherein the trifluoro compound is

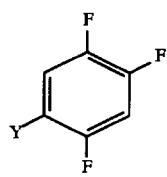

and the difluoro compound is

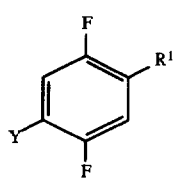

wherein all variables are as described above.

In a subclass of the invention is the process further comprising the step of reacting the difluoro compound selected from Ia, Ib or Ic with a second nucleophilic agent $R^2$ to obtain a monofluoro compound selected from

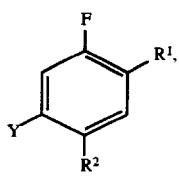

IIIa

-continued

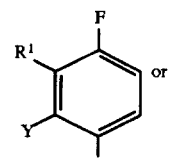

IIIb or IIIc wherein $R^2$ is selected from $OR^3$, $SR^3$, CN, C≡$CR^4$, or a 4, 5, 6 or 7-membered monocyclic nitrogen containing heterocyclic ring containing one or two nitrogen atoms; and where all other variables are as defined above.

Illustrative of the invention is the process wherein the difluoro compound is

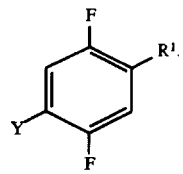   Ia and the monofluoro compound is

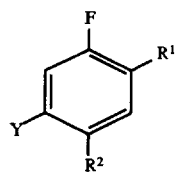   IIIa and where all variables are as described above.

Another aspect of the invention is a compound of the formula

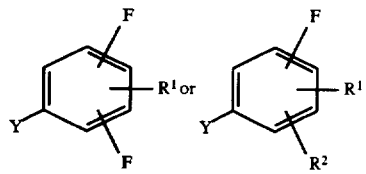

wherein Y is selected from CN, $CO_2H$ or $CO_2$—$C_{1-6}$ alkyl;
$R^1$ and $R^2$ are each independently selected from $OR^3$, $SR^3$, CN, C≡$CR^4$, or a 4, 5, 6 or 7-membered monocyclic nitrogen containing heterocyclic ring containing one or two nitrogen atoms;
$R^3$ is selected from $C_{1-10}$ alkyl, $C_{3-8}$ cycloalkyl, phenyl-$C_{1-6}$ alkyl, phenyl or a 4, 5, 6 or 7-membered monocyclic nitrogen containing heterocyclic ring containing one or two nitrogen atoms wherein the nitrogen containing heterocyclic ring is either unsubstituted or substituted with $R^5$ and $R^6$;
$R^4$ is $C_{1-10}$ alkyl;
$R^5$ and $R^6$ are each independently selected from $CO_2R^4$, $COR^4$ or $C_{1-10}$ alkyl.

In one embodiment of this aspect of the invention is the compound of the formula

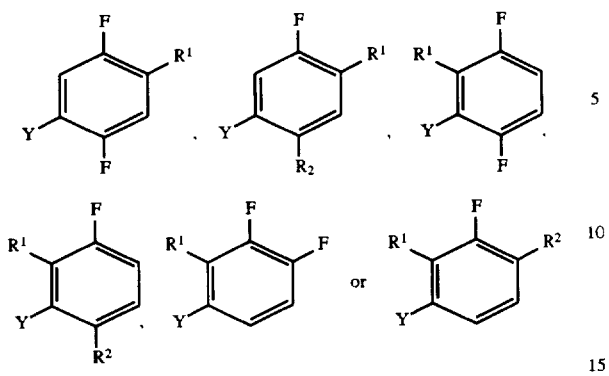
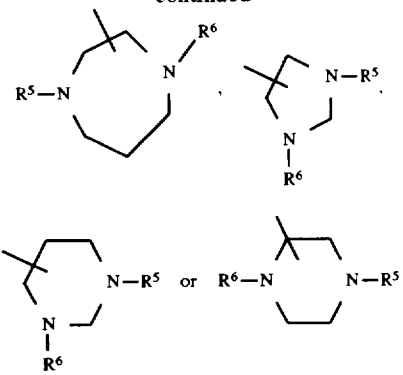

where all variables are as described above.

In a class of this aspect of the invention is the compound wherein

Y is selected from CN, $CO_2H$, $CO_2CH_3$, or $CO_2C(CH_3)_3$;
$R^1$ and $R^2$ are each independently selected from $OR^3$, $SR^3$, CN, $C\equiv CR^4$, or a heterocyclic ring selected from

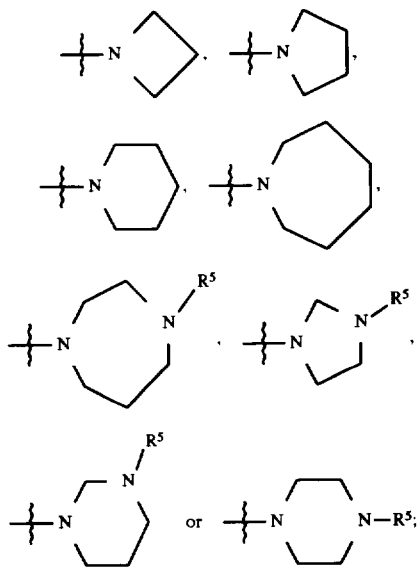

$R^3$ is selected from $C_{1-6}$ alkyl, $C_{3-6}$ cycloalkyl, benzyl, phenyl or a heterocyclic ring selected from

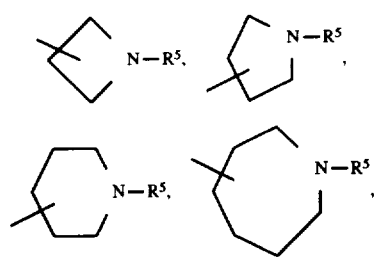

$R^4$ is $C_{1-6}$ alkyl;
$R^5$ and $R^6$ are each independently selected from $CO_2R^4$, $COR^4$ or $C_{1-6}$ alkyl.

In a subclass of this aspect of the invention is the compound of the formula

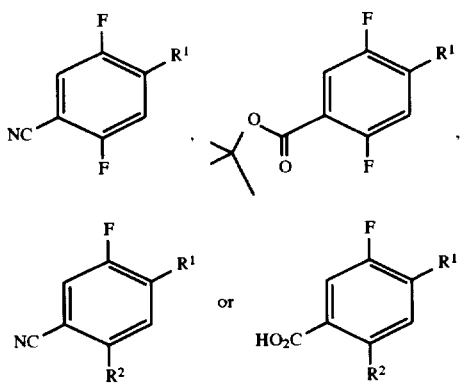

wherein $R^1$ is selected from

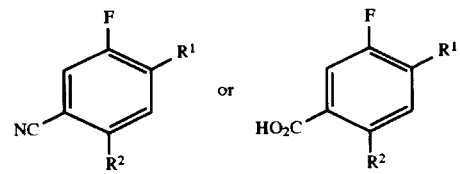

$R^2$ is selected from

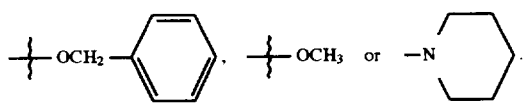

An illustration of this aspect of the invention is the compound selected from

9

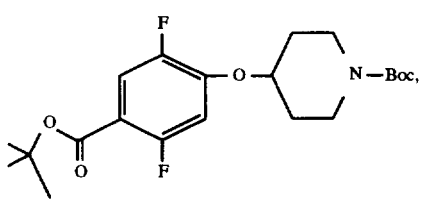

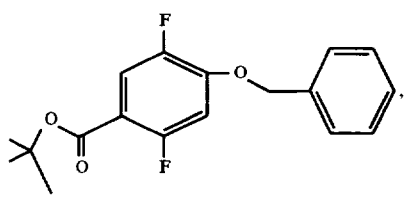

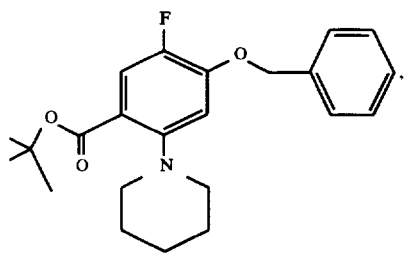

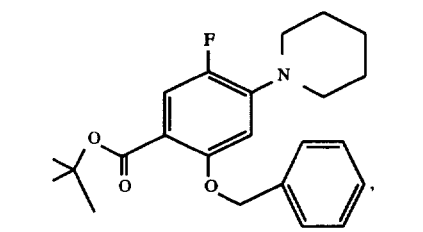

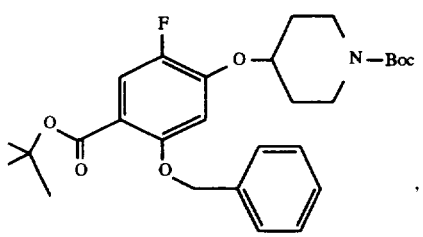

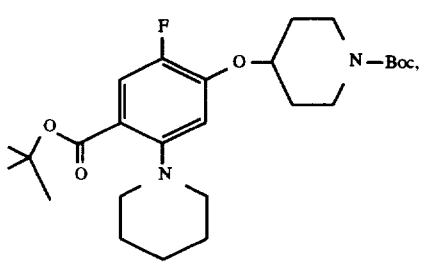

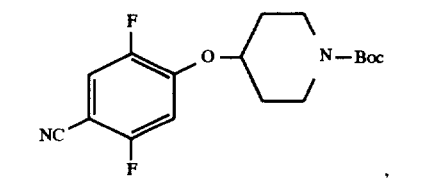

10

-continued

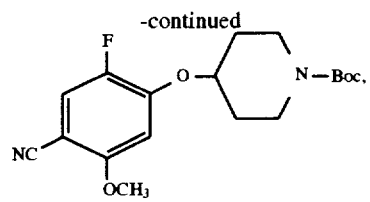

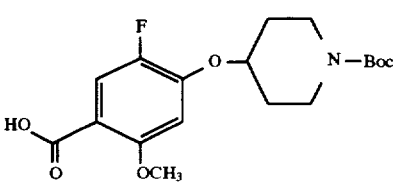

or

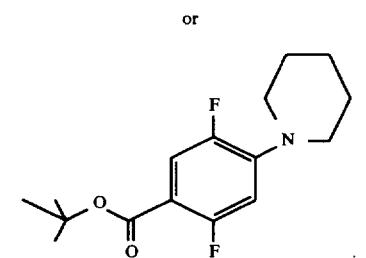

DETAILED DESCRIPTION OF THE INVENTION

The instant invention provides a process for regioselective nucleophilic substitution of trifluorobenzoate and/or trifluoronitrile. In a preferred embodiment of the present invention, 2,4,5-trifluorobenzoate/trifluorobenzonitrile is regioselectively substituted at the 4-position by a nucleophile to afford the 2,5-difluorobenzoate/difluorobenzonitrile in high yields. Preferably, the nucleophile is an oxygen nucleophile (e.g., alkoxide), a nitrogen heterocycle (e.g., piperidine), a sulfur nucleophile (e.g., thiol) or a carbon nucleophile (e.g., nitrile, acetylene). Additionally, the resultant 2,5-difluorobenzoate/difluorobenzonitrile can be subsequently substituted at the 2-position by a second nucleophile to afford the 5-fluorobenzoate/fluorobenzonitrile which is useful as an intermediate in the synthesis of fluorinated oxytocin antagonists, e.g., Compound A.

The nucleophilic substitution of trifluorobenzoate/trifluorobenzonitrile to form the difluorobenzoate/difluorobenzonitrile can be run at a temperature range of −78° to 5° C., preferably, −78° to −30° C., most preferably, about −65° C. Subsequent substitution of the difluorobenzoate/difluorobenzonitrile with a nucleophile to form the monofluorobenzoate/monofluorobenzonitrile can be run at a temperature range of −50° to 50° C., preferably, 20° to 25° C., most preferably, about 5° C.

A variety of solvents can be utilized in the nucleophilic substitution reactions of the present invention. More specifically, the nucleophilic substitution reactions of the present invention can be run in a solvent selected from a hydrocarbon solvent (e.g., hexane, cyclohexane) an aromatic solvent (e.g., toluene, benzene) or an oxygenated organic solvent (e.g., DMF, NMP, an ether). Examples of ethers which are suitable for use in the present invention include, but are not limited to, diethyl ether, tert-butyl methyl ether, and tetrahydrofuran. Preferably, an oxygenated organic solvent is utilized. Most preferably, the reaction is run using THF, DMF or NMP as the solvent.

Abbreviations used in the instant specification are as follows:

AcOH or HOAc=acetic acid
Bn=benzyl
Boc or BOC=tert-butyloxycarbonyl
DCM=dichloromethane
DEAD=diethyl azodicarboxylate
DIEA=diisopropylethylamine
DMF=N,N-dimethylformamide
DMSO=dimethylsulfoxide
EDC=1-ethyl-3-(3-dimethylaminopropyl)carbodiimide
Et=ethyl
EtOAc=ethyl acetate
EtOH=ethanol
eq.=equivalent
FAB MS=fast atom bombardment mass spectroscopy
Me=methyl
MeOH=methanol
MTBE=tert-butyl methyl ether
NMP=1-methyl-2-pyrrolidinone
Ph=phenyl
r.t.=room temperature
THF=tetrahydrofuran The compounds of the present invention, may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "cesarean delivery" shall mean incision through the abdominal and uterine walls for delivery of a fetus.

The term "alkyl," as used herein, includes both straight and branched chain alkanes of the number of carbon atoms specified (e.g., $C_{1-8}$ alkyl), or any number within this range (i.e., methyl, ethyl, 1-propyl, 2-propyl, n-butyl, s-butyl, t-butyl, etc.).

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "phenyl-$C_{1-6}$ alkyl" refers to a phenyl ring attached to a $C_{1-6}$ alkyl group, e.g., benzyl, phenylethyl, phenylpropyl, etc.

As used herein, the term "halogen" shall include, iodine, bromine, chlorine and fluorine.

The term "nitrogen heterocycle," as used herein, represents an unsubstituted or substituted stable 4- to 7-membered monocyclic saturated ring system which consists of carbon atoms and from one to two nitrogen heteroatoms; the heterocyclic ring may be attached at any heteroatom or carbon atom which results in the creation of a stable structure. Examples of such nitrogen heterocycles include, but is not limited to, piperidinyl, piperazinyl, azepinyl, pyrrolyl, pyrrolidinyl, pyrazolyl, pyrazolidinyl, imidazolyl.

The term "oxygen nucleophile," as used herein, refers to an electron pair donor resided on an oxygen atom.

The term "sulfur nucleophile," as used herein, refers to an electron pair donor resided on a sulfur atom.

The term "carbon nucleophile," as used herein, refers to an electron pair donor resided on an carbon atom.

The following examples are provided to further define the invention without, however, limiting the invention to the particulars of these examples. For the compounds of Examples 1–14, which follow, $^1$H NMR spectra were measured at 300 MHz on a Bruker AM-300 instrument, and $^{13}$C NMR spectra were run at 75.5 MHz on the same instrument. $^1$H and $^{13}$C NMR spectras for the compounds of Examples 1–14 were consistent with structures.

EXAMPLE 1

Synthesis of Difluoroester 9 from Trifluoroester 8

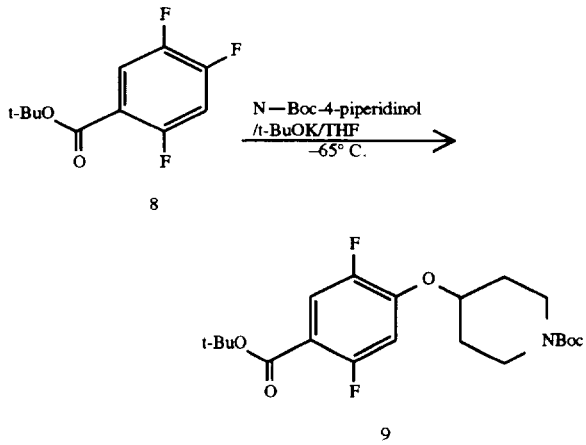

To a solution of N-Boc-4-piperidinol (1.95 g, 9.68 mmol) in THF (5.0 ml) was added a solution of t-BuOK in THF (Aldrich, 1.0M, 10.6 ml) at 0° C. and the resulting reaction mixture was stirred for 0.5 h at that temperature. The reaction mixture was slowly cannulated to a cold solution of trifluoroester 8 (2.05 g, 8.80 mmol) in THF (5.0 ml) at –65° C. and was then aged at –30° C. for 1.5 h. The reaction was quenched with water (5.0 ml) at –30° C. and then extracted with MTBE (150 ml). The organic layer was washed with water (30 ml), then brine (30.0 ml) and dried over MgSO$_4$. Evaporation of the solvents gave an oily residue. Chromatography of the residue on silica gel (eluted with 5% ethyl acetate/hexane) provided 2.31 g of the desired product 9 (63.6% yield).

EXAMPLE 2

Synthesis of Monofluoroacid 5

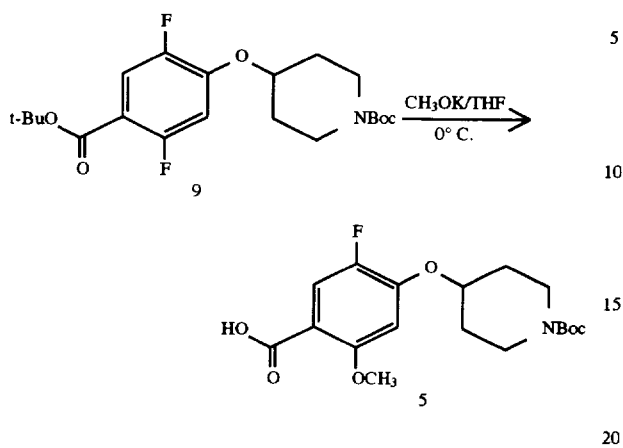

To a solution of t-BuOK in THF (1.0M, 2.0 ml) was added MeOH (0.081 ml, 2.0 mmol) at −4° C. and the resulting solution was stirred for 0.5 h. A THF solution of 9 (165 mg, 0.40 mmol) was introduced at −4° C. and the reaction mixture was stirred at 0° C. for 1.0 h. The reaction mixture was allowed to warm to 25° C. and stirred for 6 h. The reaction mixture was diluted with MTBE (25 ml) and water (25 ml) at 25° C. The aqueous layer was separated and then neutralized with 2N HCl to pH=1. The neutralized aqueous layer was extracted with $CH_2Cl_2$ (25 ml×2). The combined organic layers were washed with water (25 ml) and dried over $MgSO_4$. Evaporation of the solvent gave the solid acid 5.

EXAMPLE 3

Synthesis of Difluoronitrile 12 from Trifluoronitrile 11

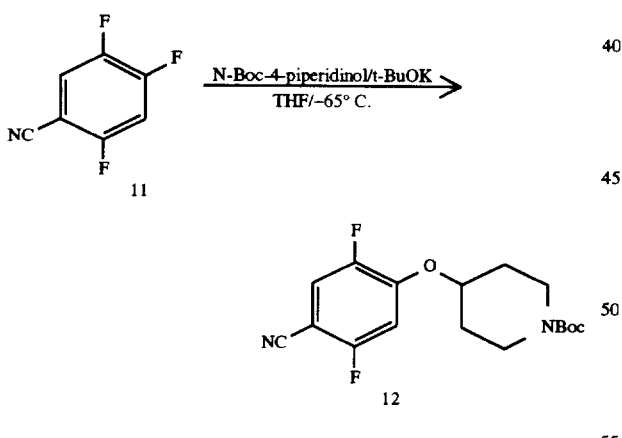

A t-BuOK solution (1.0M, 5.0 ml) was slowly added to a solution of N-Boc-4-piperidinol (1.0 g, 4.97 mmol) in THF (3.0 ml) at 5° C. and the resulting mixture stirred for 0.5 h. The mixture was then transferred to a cold solution of trifluoronitrile 11 (Aldrich, 0.569 ml, 4.97 mmol) in THF (3.0 ml) at −65° C. The reaction mixture was stirred at −65° C. for 3.0 h and then allowed to warm to 25° C. over 1.0 h. The reaction mixture was quenched with water (25 ml) and was diluted with MTBE (100 ml). The organic layer was separated and washed with water (35 ml), brine (35 ml), and dried over $MgSO_4$. Evaporation of the solvent under vacuum provided 1.65 g of a white solid 12 (99% yield).

EXAMPLE 4

Synthesis of Monofluoronitrile 13 from Difluoronitrile 12

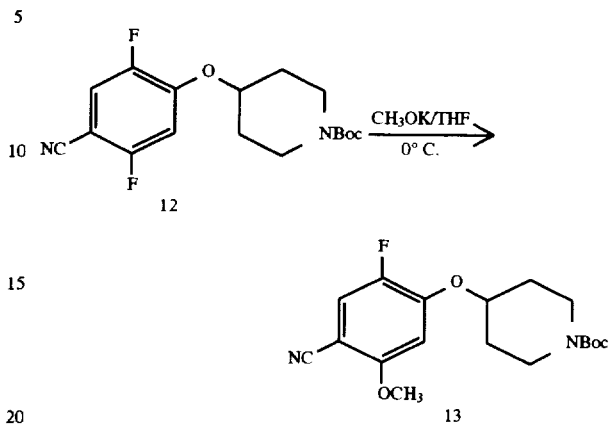

MeOH (0.151 ml, 3.73 mmol) was added to a solution of t-BuOK in THF (1.0M, 3.73 ml) at 5° C. resulting in a light suspension which was stirred for 0.5 h at 5° C. The light suspension was cannulated into a cold solution of difluoronitrile 12 (0.84 g, 2.485 mmol) in THF (3.0 ml) at −50° C. and then aged for 1.0 h at −50° C. The reaction mixture was warmed to 5° C. over 0.5 h and stirred at 5° C. for 2 h after which the reaction was quenched with water (15 ml). The reaction mixture was diluted with MTBE (100 ml), and the organic layer was washed with water (35 ml), then brine (35 ml). After drying over $MgSO_4$, the organic layer was evaporated to dryness to provide a waxy solid of monofluoronitrile 13 (0.83 g, 95% yield).

EXAMPLE 5

Synthesis of Monofluoroacid 5 from Monofluoronitrile 13

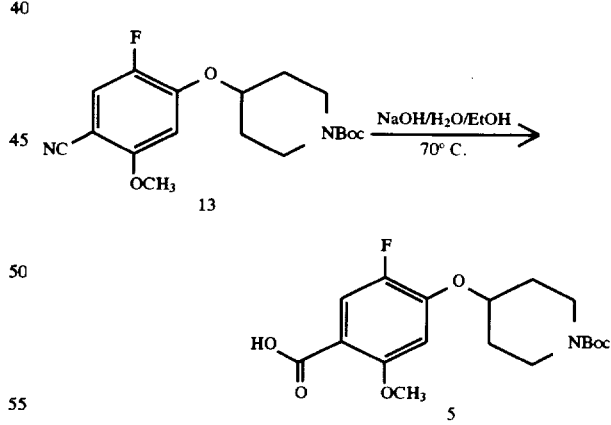

A NaOH solution (3.0 ml, 50 wt %) was added to a solution of 13 (0.416 g, 1.19 mmol) in EtOH (3.0 ml), followed by addition of water (3.0 ml) at 25° C. The resulting slurry was heated to 70° C. for 16 h and then cooled to 5° C. Conc. HCl was added at 5° C. to adjust the pH to 1, and the mixture was then extracted with ethyl acetate (100 ml). The organic layer was separated and washed with water (25 ml), brine (25 ml) and dried over $MgSO_4$. Evaporation of the solvent gave the acid 5 as a white solid (0.40 g, 90% yield).

15

EXAMPLE 6

Synthesis of Monofluoroester 14 from Difluoroester 9

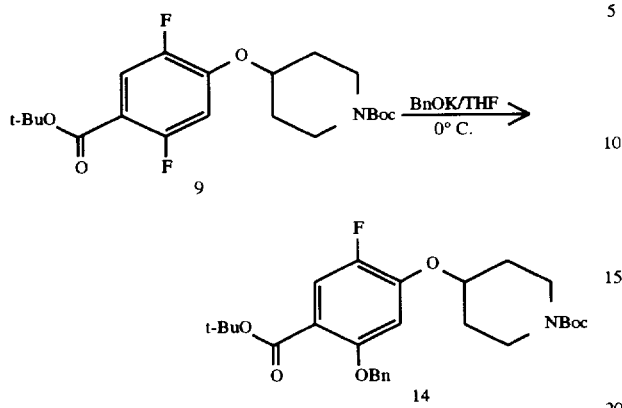

A solution of t-BuOK in THF (1.0M, 0.55 ml) was added to a solution of benzyl alcohol (0.057 ml, 0.55 mmol) in THF (2.0 ml) at 5° C. and the resulting mixture stirred at 5° C. for 0.5 h. The difluoroester 9 (206 mg, 0.5 mmol) was introduced as a solid at 5° C. and the reaction was stirred at 5° C. for 4.5 h. The reaction was warmed to 25° C. and stirred for an additional 1.5 h, then quenched with water (5.0 ml) and extracted with MTBE (50 ml). The organic layer was washed with water (15 ml), brine (15 ml) and dried over $MgSO_4$. Evaporation of the solvent afforded the desired product 14.

EXAMPLE 7

Synthesis of Monofluoroester 15 from Difluoroester 9

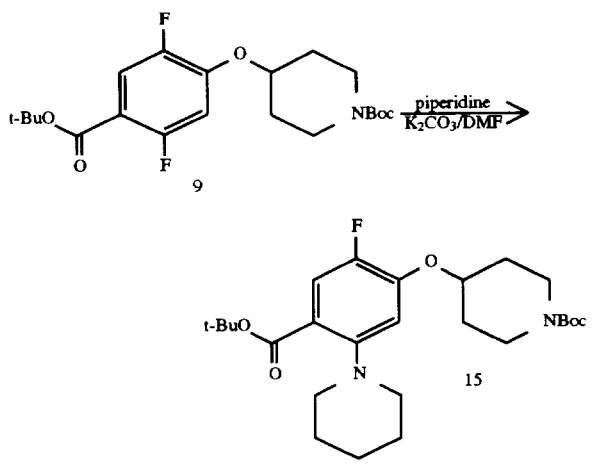

The starting material 9 (191 mg, 0.46 mmol), piperidine (0.0686 ml, 0.695 mmol) and potassium carbonate (128 mg, 0.928 mmol) were mixed together in DMF (5.0 ml) at 25° C. The slurry was stirred and heated to 110° C. for 12 h. After cooling to 25° C., the reaction mixture was diluted with water (15 ml) and extracted with MTBE (100 ml). The organic layer was separated and washed with water (25 ml×2), sat. $NaHCO_3$ (20 ml) and brine (20 ml). The organic layer was dried over $MgSO_4$ and evaporated to dryness. Chromatography of the residue on silica gel and elution with 15% ethyl acetate/hexane provided 15 in 75% yield (160 mg).

16

EXAMPLE 8

Synthesis of Difluoroesters 16a and 16b from Trifluoroester 8

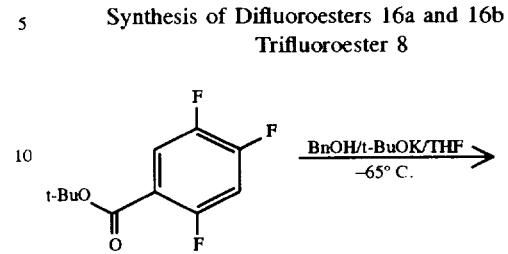

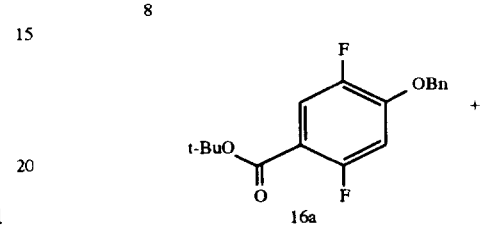

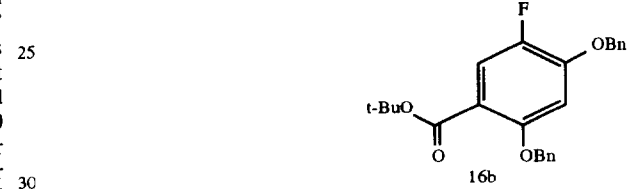

A solution of t-BuOK in THF (1.0M, 1.06 ml) was added to a solution of benzyl alcohol (0.11 ml, 1.06 mmol) in THF (2.0 ml) at 5° C. and the resulting mixture stirred at 5° C. for 0.5 h. A solution of 8 (205.4 mg, 0.88 mmol) in THF (2.0 ml) was introduced slowly at 5° C. and kept at 5° C. for 3.5 h. The reaction was warmed to 25° C. for 0.5 h, and then the reaction was quenched with water and diluted with MTBE (100 ml). The organic layer was separated and washed with water (25 ml) and brine (25 ml), followed by drying over $MgSO_4$. Evaporation of the solvent gave a residue which was chromatographed on silica gel. Elution with 5% ethyl acetate/hexane gave a first fraction containing difluoroester 16a (114 mg, 40.5% yield) and a second fraction containing monofluoroester 16b (107 mg, 29.8% yield).

EXAMPLE 9

Synthesis of Monofluoroester 17 from Difluoroester 16a

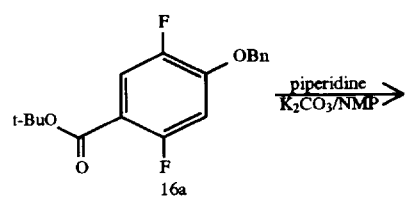

17

-continued

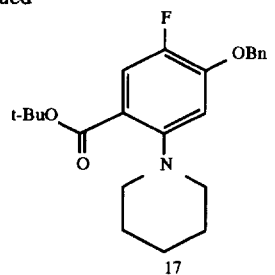

Piperidine (0.077 ml, 0.78 mmol) was added to a solution of difluoroester 16a (100 mg, 0.31 mmol) in THF (2.0 ml) at 25° C., followed by addition of $K_2CO_3$ (86 mg, 0.62 mmol). The resulting suspension was stirred at 25° C. for 2.0 h and then heated to reflux for 2.0 h. To this slurry was added NMP (2.0 ml) and refluxing continued for 12 h. The reaction mixture was diluted with water (10 ml) and extracted with MTBE (100 ml). The organic layer was separated and washed with water (25 ml×2), sat. $NaHCO_3$ (25 ml) and brine (25 ml). After drying over $MgSO_4$, the solvent was removed under vacuum to give the product 17.

EXAMPLE 10

Synthesis of Difluoroester 18 from Trifluoroester 8

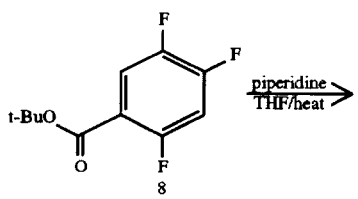

Piperidine (0.80 ml, 8.09 mmol) was added to a solution of trifluoroester 8 (0.84 g, 3.61 mmol) in THF (5.0 ml) at 25° C. and the reaction mixture stirred for 1.0 h. The mixture was heated to reflux for 2 h, and then cooled to 25° C. The reaction mixture was diluted with water (35 ml) and extracted with MTBE (150 ml). The organic layer was washed with sat. $NaHCO_3$ (35 ml), brine (35 ml) and dried over $MgSO_4$. Evaporation of the solvent gave the desired product 18 as an oil (1.04 g, 96.7% yield).

18

EXAMPLE 11

Synthesis of Monofluoroester 19 from Difluoroester 18

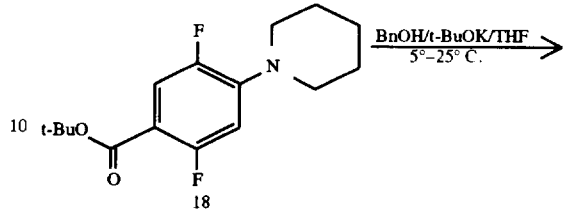

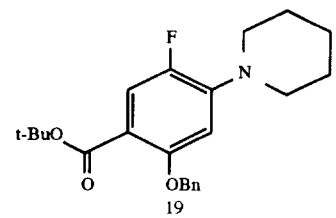

Benzyl alcohol (0.187 ml, 1.81 mmol) was added to a solution of t-BuOK in THF (1.0M, 1.81 ml) at 5° C. and the resulting solution stirred for 0.5 h at that temperature. To this solution was added a solution of difluoroester 18 (538 mg, 1.81 mmol) in THF (2.0 ml) at 5° C. over 10 min. The resulting solution was kept at 5° C. for 1.5 h, then warmed to 25° C., and stirring continued for 2.0 h. The reaction was quenched with water (5.0 ml) at 25° C. and extracted with MTBE (150 ml). The organic layer was washed with water (25 ml) and brine (25 ml). After drying over $MgSO_4$, the solvent was evaporated to give a residue which was chromatographed on silica gel and eluted with 10% ethyl acetate/hexane. Concentration of the appropriate fractions gave the desired product 19 which was obtained as an oil (0.5 g, 70.4% yield).

EXAMPLE 12

Synthesis of Difluoronitrile 21 from Trifluoronitrile 20

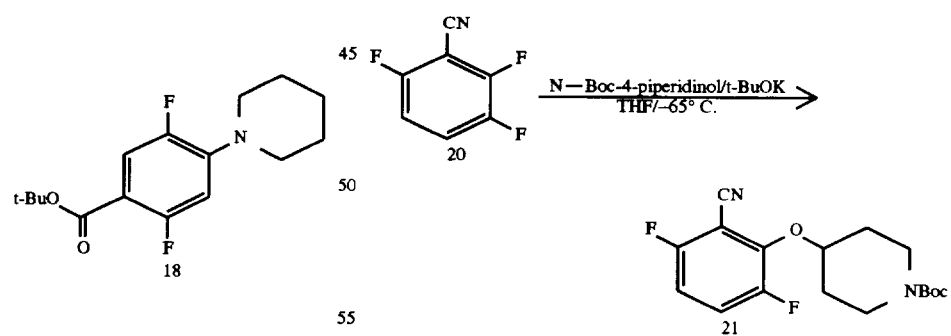

A solution of t-BuOK in THF (1.0M, 3.18 ml) was added to a solution of N-Boc-4-piperidinol (0.64 g, 3.18 mmol) in THF (2.0 ml) at 5° C. and the resulting solution stirred for 0.5 h at 5° C. The resulting solution was then slowly cannulated to a solution of trifluoronitrile 20 (Aldrich, 0.364 ml, 3.18 mmol) in THF (2.0 ml) at −65° C. The reaction was stirred at −65° C. for 3.0 h. Water (5.0 ml) was added to quench the reaction at −65° C. and then the mixture was warmed to 25° C. and extracted with MTBE (150 ml). The organic layer was separated and washed with water (25 ml)

and brine (25 ml). After drying over MgSO₄, the solvent was removed under vacuum to provide the product 21 as a white solid which was used, without further purification, in the next step.

EXAMPLE 13

Synthesis of Monofluoronitrile 22b from Difluoronitrile 21

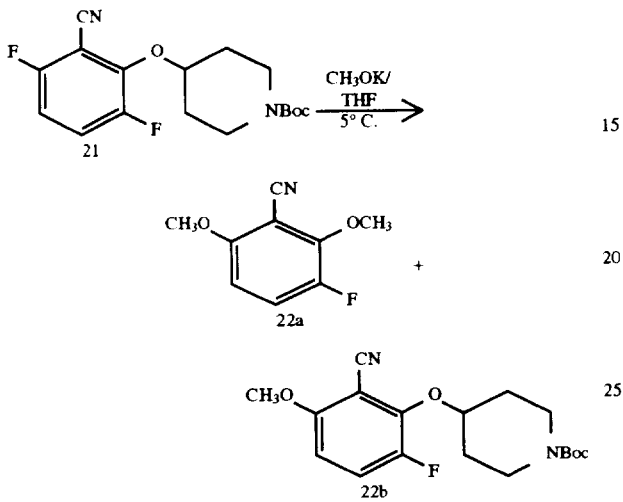

MeOH (0.258 ml, 6.36 mmol) was added to a solution of t-BuOK in THF (1.0M, 6.36 ml) at 5° C. and the resulting light slurry was stirred at 5° C. for 0.5 h. The slurry was slowly transferred to a cold solution of 21 (estimated: 3.18 mmol) in THF (4.0 ml) at −56° C. and stirred at that temperature for 2 h. The reaction was warmed to 5° C. and kept at that temperature for 4 h. The reaction was quenched with water (5.0 ml) at 5° C. and extracted with MTBE (150 ml). The organic layer was washed with water (25 ml), brine (25 ml) and dried over MgSO₄. Evaporation of the solvent afforded a residue which was chromatographed on silica gel. Elution with 15% ethyl acetate/hexane gave a first fraction containing product 22a and a second fraction containing the desired product 22b.

EXAMPLE 14

Synthesis of Difluoronitrile 24 from Trifluoronitrile 23

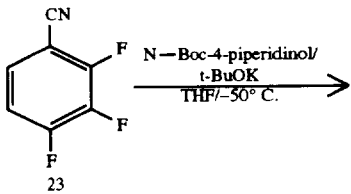

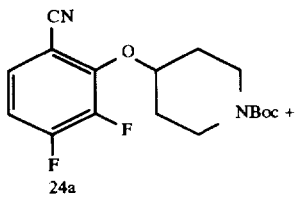

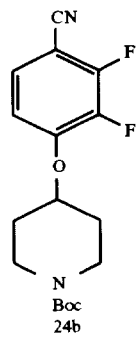

A solution of t-BuOK in THF (1.0M, 6.30 ml) was added to a solution of N-Boc-4-piperidinol (1.23 g, 6.1 mmol) in THF (4.0 ml) at −40° C. and the resulting solution stirred for 0.5 h at −40° C. The resulting solution was slowly cannulated to a solution of trifluoronitrile 23 (Aldrich, 0.364 ml, 3.18 mmol) in THF (4.0 ml) at −50° C. The reaction was stirred at −50° C. for 0.5 h. Water (5.0 ml) was added to quench the reaction at −50° C. and the reaction was then warmed to 25° C. The reaction mixture was extracted with MTBE (150 ml) and the organic layer was separated, washed with water (25 ml) and dried over MgSO₄. The organic layer was evaporated to give a residue which was chromatographed on silica gel. Elution with 15% ethyl acetate/hexane gave a first fraction containing product 24a (64%) and a second fraction containing product 24b (14%)

Compound A was prepared from Monofluoroacid 5 according to Examples 15 to 17 which follow. For examples 15–17 which follow. ¹H NMR spectra were measured at 300 MHz on a Varian XL-300, at 400 MHz on a Varian XL-400 and at 360 MHz on a Nicolet NT-360 using (CH₃)₄Si as an internal standard and Fast atom bombardment mass spectra (FAB MS) were obtained on a VG-ZAB-HF spectrometer All NMRs for the compounds of Examples 15–17 which follow were consistent with structures.

EXAMPLE 15

1-(1-(4-(N-tert-butyloxycarbonyl-4-piperidinyloxy)-5-fluoro-2-methoxybenzoyl)piperidin-4-yl)-4H-3,1-benzoxazin-2(1H)-one

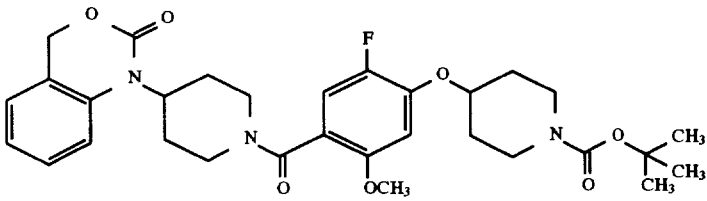

Step 1: 1-t-Butyloxycarbonyl-4-piperidinone (20 g, 0.10 mol), 2-aminobenzyl alcohol (13 g, 0.11 mol), and acetic acid (14 mL, 0.22 mol) were dissolved in dry toluene (500 mL). The solution was refluxed under inert atmosphere for 3 h with azeotropic removal of water. The solution was cooled to ambient temperature and concentrated under reduced pressure to one half of the original volume. To the solution was added NaBH$_3$CN (20 g, 0.32 mol) and dry THF (300 mL). Acetic acid (10 mL, 0.15 mmol) was added dropwise over a period of about 1 h. The reaction was stirred at ambient temperature for 24 h. The mixture was concentrated under reduced pressure and the residue was dissolved in EtOAc (750 mL). The EtOAc layer was washed with saturated aqueous NaHCO$_3$ (3×500 mL) and brine (250 mL). The EtOAc layer was dried (MgSO$_4$), filtered, and the solvent was removed under reduced pressure. The residue was purified by pressurized silica gel column chromatography, using a gradient elution of 15–30% EtOAc-hexanes. 1-t-Butyloxycarbonyl-4-((2-hydroxymethyl)phenylamino)piperidine was obtained as a gum (TLC: R$_f$=0.30 (30:70 EtOAc:hexanes); HPLC (method A) retention time=8.89 min).

Step 2: 1-t-Butyloxycarbonyl-4-((2-hydroxymethyl)phenylamino)piperidine (24 g, 78 mmol) from Step 1 above was dissolved in dry THF (250 mL) and cooled to 0° C. under an atmosphere of nitrogen. To the solution was added DIEA (41 mL, 0.24 mol) and triphosgene (8.54 g, 28.8 mmol). The reaction was stirred at 0° C. for 1 h, and then at ambient temperature for 24 h. Ether (250 mL) was added, the mixture was cooled to 0° C. and then filtered to remove the hydrochloride salt of DIEA. The filtrate solvents were removed under reduced pressure and the residue was dissolved in EtOAc (750 mL). The EtOAc solution was washed with 5% aqueous citric acid (2×500 mL), water (250 mL), and saturated aqueous NaHCO$_3$ (2×500 mL). The EtOAc layer was dried (MgSO$_4$), filtered, and the solvent was removed under reduced pressure. The residue was boiled in ether (ca. 200 mL) until the solid had dissolved. Cooling overnight gave 1-(N-t-butyloxycarbonyl-4-piperidinyl)-4H-3,1-benzoxazin-2(1H)-one as off-white crystals, mp 143°–145° C. (TLC: R$_f$=0.28 (30:70 EtOAc:hexanes); HPLC (method A) retention time =8.77 min; FAB MS: m/z 333 (M$^+$+H)).

Step 3: A stirred solution of 1-N-t-butyloxycarbonyl-4-piperidinyl)-4H-3,1-benzoxazin-2(1H)-one (19 g, 57 mmol) from Step 2 above in EtOAc (500 mL) was cooled to 0° C. HCl gas was bubbled through the solution for 30 min. Stirring was continued at 0° C. for 1 h, during which time a precipitate had formed, and the reaction was warmed to ambient temperature for 1 h. The stirred suspension was cooled to 0° C. and cold ether (250 mL) was added. The precipitate was collected by filtration and washed with ether. The solid was dried under reduced pressure for 18 h, giving 1-(4-piperidinyl)-4H-3,1-benzoxazin-2(1H)-one hydrochloride as a white amorphous solid (TLC: R$_f$=0.29 (90:10:1 CH$_2$Cl$_2$:MeOH:NH$_4$OH); HPLC (method A) retention time=3.88 min; FAB MS: m/z 233 (M$^+$+H)).

Step 4: To a solution of the hydrochloride salt of 1-(4-piperidinyl)-4(H)-3,1-benzoxazin-2(1H)-one (150 mg, 0.56 mmol) from Step 3 above in DMF (5 mL) was added 4-(N-tert-butyloxycarbonyl-4-piperidinyloxy)-5-fluoro-2-methoxybenzoic acid, 5 (206 mg, 0.56 mmol), HOBT (92 mg, 0.60 mmol), and EDC (140 mg, 0.73 mmol). To the stirred solution was added DIEA (0.19 mL, 1.1 mmol) until the reaction was pH 7 as judged by spotting an aliquot on wetted E. Merck "colorpHast" pH 1–14 indicator strips. The reaction was stirred at ambient temperature for 18 h and the solvent was removed under reduced pressure. The residue was dissolved in EtOAc (50 mL) and washed with 5% aqueous citric acid (25 mL), water (25 mL), and saturated aqueous NaHCO$_3$ (25 mL). The EtOAc layer was dried (MgSO$_4$), filtered, and the solvent was removed under reduced pressure. The residue was purified by pressurized silica gel column chromatography using a gradient elution of 1–3% MeOH—CHCl$_3$. The title compound, 1-(1-(4-(N-tert-butyloxycarbonyl-4-piperidinyloxy)-5-fluoro-2-methoxybenzoyl)piperidin-4-yl)-4H-3,1-benzoxazin-2(1H)-one was obtained as an amorphous solid.

Analysis calculated for C$_{31}$H$_{38}$FN$_3$O$_7$, 0.2 EtOAc, 0.25 H$_2$O C, 63.04; H, 6.67; N, 6.94 Found: C, 63.06; H, 6.56; N, 6.93

TLC: R$_f$=0.17 (4:1 EtOAc:hexanes)

HPLC (method A) retention time=9.8 min

FAB MS m/z 584 (M$^+$+H)

EXAMPLE 16

1-(1-(4-(4-piperidinyloxy)-5-fluoro-2-methoxybenzoyl)piperidin-4-yl)-4H-3,1-benzoxazin-2(1H)-one

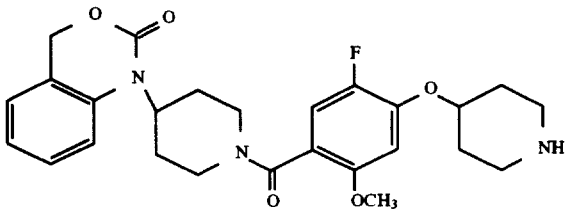

1(1-(4-(N-tert-butyloxycarbonyl-4-piperidinyloxy)-5-fluoro-2-methoxybenzoyl)piperidin-4-yl)-4H-3,1-benzoxazin-2(1H)-one from Example 15 was converted to the title compound using a procedure analogous to that given in Step 3 of Example 15. The hydrochloride salt of 1-(1-(4-

(4-piperidinyloxy)-5-fluoro-2-methoxybenzoyl)piperidin-4-yl)-4H-3,1-benzoxazin-2(1H)-one was obtained as an amorphous solid.

Analysis calculated for C$_{26}$H$_{30}$FN$_3$O$_5$, 2.0 HCl, 0.15 EtOAc C, 56.08; H, 5.87; N, 7.38 Found: C, 56.02; H, 5.94; N, 7.37

TLC: R$_f$=0.12 (96:4:0.4 CH$_2$Cl$_2$:MeOH:NH$_4$OH)
HPLC (method A) retention time=6.2 min
FAB MS m/z 484 (M$^+$+H)

EXAMPLE 17

1-(1-(4-(N-acetyl-4-piperidinyloxy)-5-fluoro-2-methoxybenzoyl)piperidin-4-yl)-4H-3,1-benzoxazin-2(1H)-one, Compound A

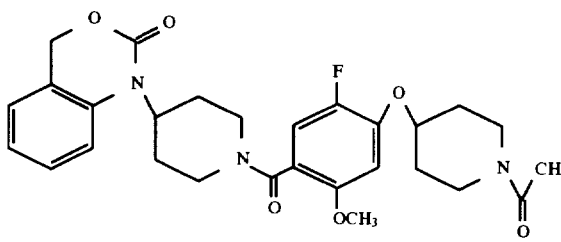

To a stirred solution of 1-(1-(4-(4-piperidinyloxy)-5-fluoro-2-methoxybenzoyl)piperidin-4-yl)-4H-3,1-benzoxazin-2(1H)-one of Example 16 (200 mg, 0.41 mmol) in DCM (5 mL) at ambient temperature was added acetic anhydride (77 mg, 0.75 mmol) and DIEA (0.17 mL, 1.0 mmol). The solution was stirred at ambient temperature for 24 h, diluted with DCM (20 mL), washed with saturated aqueous NaHCO$_3$ (50 mL), dried (MgSO$_4$), and filtered. The solvent was removed under reduced pressure and the residue was purified by pressurized silica gel column chromatography using a gradient elution of 2–5% MeOH-DCM. 1-(1-(4-(N-acetyl-4-piperidinyloxy)-5-fluoro-2-methoxybenzoyl)piperidin-4-yl)-4H-3,1-benzoxazin-2(1H)-one was obtained as an amorphous solid.

Analysis calculated for C$_{28}$H$_{32}$FN$_3$O$_6$, 0.45 EtOAc, 0.65 H$_2$O C, 62.03; H, 6.45; N, 7.28 Found: C, 62.02; H, 6.22; N, 7.26

TLC: R$_f$=0.33 (97:3 CH$_2$Cl$_2$:MeOH)
HPLC (method A) retention time=7.4 min
FAB MS m/z 526 (M$^+$+H)

While the foregoing specification teaches the principles of the present invention, with examples for the purpose of illustration, it will be understood that the practice of the invention encompasses all of the usual variations, adaptations and/or modifications as come within the scope of the following claims and their equivalents.

What is claimed is:

1. A compound of the formula

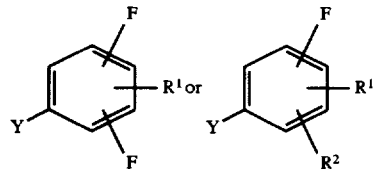

wherein Y is selected from CN, CO$_2$H or CO$_2$—C$_{1-6}$ alkyl;
R$^1$ and R$^2$ are each independently selected from OR$^3$, SR$^3$, or a 6-membered monocyclic nitrogen containing heterocyclic ring containing one nitrogen atom;

R$^3$ is 6-membered monocyclic nitrogen containing heterocyclic ring containing one nitrogen atom wherein the nitrogen containing heterocyclic ring is either unsubstituted or substituted with R$^5$ and R$^6$;

R$^4$ is C$_{1-10}$ alkyl;

R$^5$ and R$^6$ are each independently selected from CO$_2$R$^4$, COR$^4$ or C$_{1-10}$ alkyl.

2. The compound of claim 1 of the formula

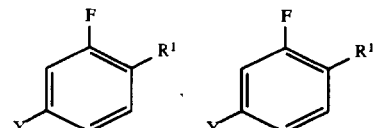

3. The compound of claim 2, wherein

Y is selected from CN, CO$_2$H, CO$_2$CH$_3$, or CO$_2$C(CH$_3$)$_3$;

R$^1$ and R$^2$ are each independently selected from OR$^3$, SR$^3$ or

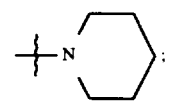

R$^3$ is

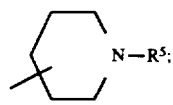

R$^4$ is C$_{1-6}$ alkyl;

R$^5$ is selected from CO$_2$R$^4$, COR$^4$ or C$_{1-6}$ alkyl.

4. The compound of claim 3 of the formula

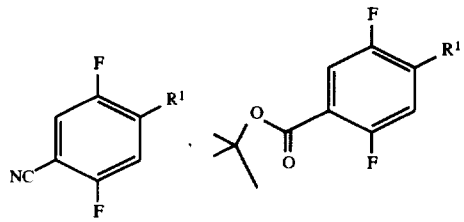

-continued
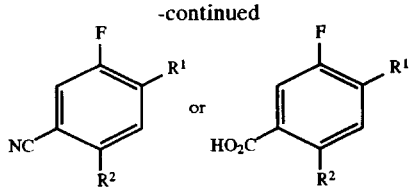
wherein R¹ is selected from
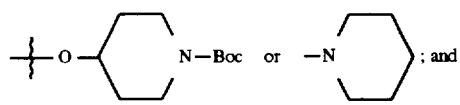
R² is selected from
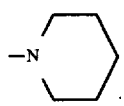
5. The compound of claim 4, selected from
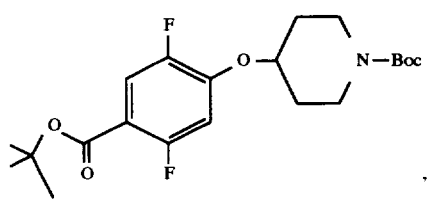
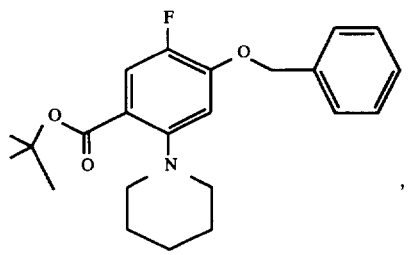
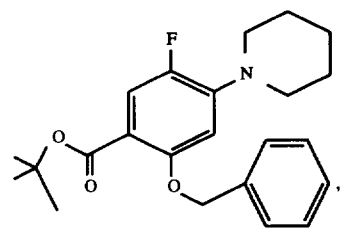
-continued
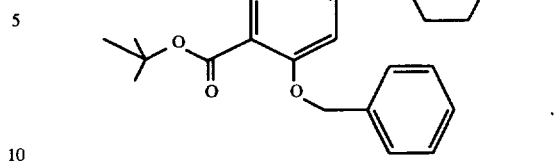
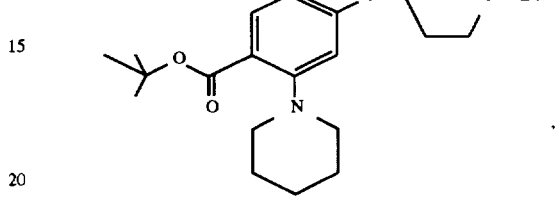
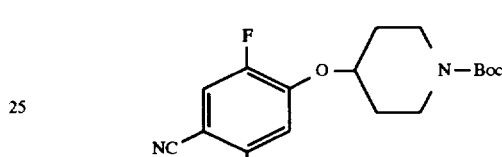
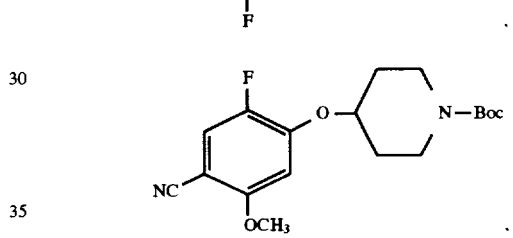
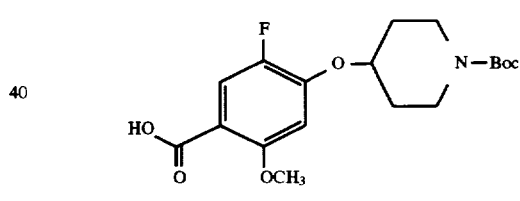
or
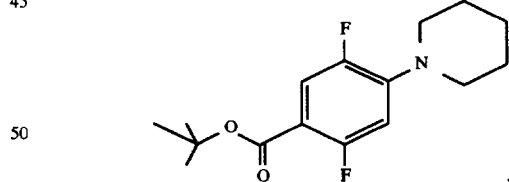
* * * * *